United States Patent [19]

Kieff et al.

[11] Patent Number: 4,707,358

[45] Date of Patent: Nov. 17, 1987

[54] VACCINE AGAINST EPSTEIN-BARR VIRUS

[75] Inventors: Elliott Kieff; Jerome Tanner; Mary Hummel; Christopher Beisel, all of Chicago, Ill.

[73] Assignee: The University of Chicago, Chicago, Ill.

[21] Appl. No.: 633,558

[22] Filed: Jul. 23, 1984

Related U.S. Application Data

[63] Continuation-in-part of Ser. No. 575,352, Jan. 30, 1984.

[51] Int. Cl.$^4$ .................. A61K 39/245; A61K 37/02; C07K 13/00
[52] U.S. Cl. ........................................ 424/89; 514/12; 530/350
[58] Field of Search ................................. 424/88, 89; 260/112.5 R; 435/68, 122.3; 514/12, 2; 530/350

[56] References Cited

PUBLICATIONS

Thorley-Lawson et al., Proc. Natl. Acad. Sci., vol. 77, pp. 5307–5311, 1980.
Hoffman et al., Proc. Natl. Acad. Sci., vol. 77, pp. 2979–2983, 1980.
Thorley-Lawson et al., J. Virol., vol. 43, pp. 730–736, 1982.
Hummel et al., J. Virol., vol. 49, pp. 413–417, 1984.
Chemical Abstracts, vol. 94, Abstract No. 137591d, 1981.
Chemical Abstracts, vol. 92, Abstract No. 74191y, 1980.

*Primary Examiner*—Blondel Hazel
*Attorney, Agent, or Firm*—Donald J. Perrella; Hesna J. Pfeiffer

[57] ABSTRACT

The nucleotide sequence of Epstein-Barr Virus (EBV) DNA which codes for outer surface viral proteins has been determined. Fragments of the DNA have been isolated and cloned into a vector which, when placed in a host organism, express proteins which when used to immunize rabbits generate antibody which reacts with the surface proteins of virus infected cells. These proteins are useful for preparation of a vaccine for EBV.

2 Claims, No Drawings

VACCINE AGAINST EPSTEIN-BARR VIRUS

RELATED APPLICATION

This application is a continuation-in-part of our co-pending application Ser. No. 575,352 filed Jan. 30, 1984.

BACKGROUND OF THE INVENTION

Infectious mononucleosis is caused by the Epstein-Barr virus (EBV), a member of the herpes virus group. The disease occurs in persons with no prior EBV antibodies. EBV-specific antibodies can be demonstrated early after onset. Antibody titers decline during convalescence, but remain detectable for life, correlating with immunity to the disease. The virus is regularly present in the oropharyngeal secretions of patients with infectious mononucleosis and often persists for months after acute disease. As with other herpes-group viruses, a persistent carrier state follows primary EBV infection.

The disease is spread through close contact, mainly by oral secretions. In areas of poor sanitation and hygiene, primary EBV infections usually occur in infancy and are silent or too mild to be diagnosed. In higher socioeconomic groups, primary exposure to EBV is often delayed until adolescence or later, when infections usually lead to typical infectious mononucleosis.

The fact the EBV transforms lymphocytes into rapidly dividing cells indicates that it may be oncogenic. There is strong evidence that EBV is involved in the etiology of Burkitt's lymphoma and nasopharyngeal carcinoma.

EBV has two high molecular weight glycoproteins on its surface (gp 350/300 and gp 220/200) and smaller amounts of other glycoproteins including a gp 85. Monoclonal antibodies and polyclonal antibodies to the gp 350/300 and gp 220/200 proteins neutralize virus infectivity.

Monoclonal antibodies frequently react with both gp 350 and gp 220. These two proteins are known to have common peptide substituents. Immunization of primates with gp 350 and gp 220 prevents infection on challenge with virus. There is also published evidence that these proteins are responsible for the specific adsorption of Epstein-Barr virus to the surface of immunoglobulin producing lymphocytes.

OBJECTS OF THE INVENTION

It is an object of the present invention to provide antigens which will prevent diseases associated with EBV infections, and which can be used diagnostically to measure EBV antibody titers and diagnose diseases associated with EBV infection. Another object is to provide methods for the preparation of these antigens. A further object is to provide compositions for administering these antigens as a vaccine. Still another object is to provide a method of using the antigens of the present invention as immunogens to raise antibodies, both in vivo and in vitro, to EBV. Yet another object is to provide a method of employing these antigens as stimulators of B lymphocyte proliferation. Another object is to provide adducts of the antigens of the present invention with therapeutic or diagnostic agents which adducts are targeted to B lymphocytes. A further object is to provide methods using the antigens of the present invention to identify and purify B lymphocytes, and to purify antibodies or immune cells which have specific reactivity with these antigens. Another object is to describe the full sequence of protein antigens which will include peptide antigens which may be synthesized by other means or expressed in other vectors. These and other objects of the present invention will be apparent from the following description.

SUMMARY OF THE INVENTION

The nucleotide sequence of Epstein-Barr virus (EBV) DNA which codes for the gp 220/200 and the gp 350/300 outer surface viral proteins has been determined. The reading frame for translation of the DNA into the gp 350/300 and gp 220/200 proteins has been established. Fragments of the DNA have been isolated and cloned into a vector which, when placed in a host organism, expresses proteins which react with neutralizing antibodies to infectious virus and with antibodies to gp 350 and gp 220. Furthermore, the expressed proteins induce antibodies in rabbits which react with gp 350 and gp 220 on the surface of virus, on virus infected cells, and as solubilized proteins. The expressed proteins are useful for preparation of a vaccine for EBV.

DETAILED DESCRIPTION OF THE INVENTION

The present invention is directed to identification of the EBV DNA which encodes the protective immunogenic proteins gp 350 and gp 220. More specifically, it is directed to a 2.8 kb DNA fragment whose nucleotide sequence and amino acid sequence are disclosed.

The present invention is also directed to vectors containing all or part of this 2.8 kb DNA fragment. A suitable vector, is for example, the B-galactosidase expression vector pMC 1511.

The present invention is also directed to host cells which contain these vectors and which cells are capable of expressing all or part of the peptides coded for by the 2.8 kb DNA fragment. In accordance with known techniques, it would be obvious to those skilled in the art that parts of the foregoing peptides could be chemically synthesized or modified and retain their immunogenicity. The present invention is therefore also directed toward chemical synthesis of domains of these proteins, especially domains including and surrounding hydrophilic regions and threonine or serine and asparginine-X-serine or threonine residues since these domains are likely to reside on the outer surface of the virus.

RNAs are isolated from cells producing EBV. These RNAs are preselected by hybridization to the Bam HIL DNA fragment and translated in vitro. The polypeptide products are immunoprecipitated with antibody specific for EBV membrane antigens. The Bam HIL fragment selected RNAs which translate the 135 and 100 kd precursors, respectively, of the gp 350/300 and gp 220/200 neutralizing antigens. Characterization of these RNAs shows that the 3.4 kb Bam HIL RNA encodes the 135 kd precursor protein and the 2.8 kb RNA encodes the 100 kd precursor protein.

The Bam HIL DNA sequence which encodes the 3.4 and 2.8 kb RNAs is precisely defined by hybridization of RNA from EBV producing cells to separated strands of Bam HIL DNA and to M13 clones of single strand segments of Bam HIL DNA. The RNAs hybridize to a 2.8 kb EBV DNA segment of the L strand of EBV DNA. The 3.4 kb RNA is encoded by the 2.8 kb DNA segment while the 2.8 kb RNA is encoded by the same segment from which a 600 nucleotide intron is spliced out.

The nucleotide sequence of these segments is determined by base sequencing analysis from which the corresponding amino acids are determined.

These segments are cloned into an appropriate expression vector which is inserted into *E. coli* a suitable host, and recombinant clones are selected which express hybrid proteins containing EBV proteins. These hybrid proteins are characterized with respect to their size and sequence and are found to react with human sera containing neutralizing antibodies which react with the gp 350/300 and gp 220/200 EBV membrane antigens. A hybrid protein has been used to immunize rabbits. The rabbit antiserum reacts with gp 350 and gp 220 and with these proteins on the surface of virus infected cells. Examples of suitable hosts for expression of EBV proteins include prokaryotic organisms such as *E. coli* and *B. subtilis,* and eukaryotic organisms such as Saccharomyces and continuous mammalian cell lines including Chinese Hamster Ovary cells or Vero cells and diploid mammalian fibroblasts including Wl 38 or MRC5 cells.

These proteins are useful individually or in combination when placed in a physiologically acceptable carrier, e.g., saline or phosphate buffered saline, to protect against EBV disease when administered to a susceptible mammalian species in amount of from about 5 to about 150 μg per dose, preferably from about 5 to about 50 μg per dose. One or more doses may be administered to produce effective protection from EBV disease. The protein may be administered by injection, for example, intramuscularly or subcutaneously. It is also to be understood that these proteins can be directly expressed in humans by means of appropriate expression vectors such as vaccinia, adeno, or herpes simplex viruses or other herpes viruses.

The following examples illustrate the present invention without, however, limiting the same thereto. The disclosure of each reference mentioned in the following examples is hereby incorporated by reference.

EXAMPLE 1

Preparation of 3.4 kb and 2.8 kb RNAs which Encode Precursor Proteins to Glycoproteins 350 and 220

Cytoplasmic polyadenylated RNAs were prepared from cells replicating EBV (B95-8 and P3Hr-1 cells induced with TPA) as previously described (J. Virol. 43: 262-272, 1982). The RNAs encoded by the EBV DNA Bam HIL fragment were selected by hybridization to cloned EBV DNA (PNAS 77: 2999-3003, 1980) covalently bound to paper (Nucl. Acids Res. 6: 195-203, 1979). These RNAs were translated in a rabbit reticulocyte lysate as previously described (PNAS 79: 5698-5702, 1982; J. Virol. 47: 193-201, 1983). The polypeptide products were preabsorbed with normal rabbit serum and immunoprecipitated with an antibody specific for the 350/300 and the 200/200 EBV membrane antigens (J. Virol. 43: 730-736, 1982) as previously described (PNAS 79: 5698-5702, 1982; J. Virol. 47: 193-201, 1982). The Bam HIL fragment selects RNAs which include those which translate the 135 and 100 kd precursors, respectively, of the gp 350/300 and gp 220/200 (J. Virol. 46: 547-556, 1983).

The RNAs which encode the 135 and 100 kd precursor proteins to glycoproteins, gp 350/300 and 220/200, respectively, were identified by size fractionating RNA through agarose gels containing methyl mercury (Anal. Biochem. 70: 75-85, 1976). One hundred fifty micrograms of B95-8 polyadenylated RNA was loaded onto a 0.8% HGT-P agarose gel (1 cm diameter, 10 cm long) and electrophoresed at 75 v for 10 hours. All chemicals and apparatus were treated with diethylpyrocarbonate before use. Fractions were collected from the bottom of the gel so that RNAs differing by approximately 200 bases were separated. B-Mercaptoethanol was added to a final concentration of 50 mM. The fractions were analyzed for the presence of Bam HIL RNAs by blot hybridization (J. Virol. 43: 262-272, 1982). Appropriate fractions were pooled, adjusted to a concentration of 0.4M NaCl, 20 mM Tris, pH 7.4, 0.2% SDS and 2 mM EDTA. Polyadenylated RNA was separated (J. Virol. 43: 262-272, 1983), translated in vitro and the polypeptide products were immunoprecipitated as in Example 2. A 3.4 kb Bam HIL RNA was identified to encode the 135 kd precursor protein to gp 350/300 and a 2.8 kb RNA was identified to encode the 100 kd precursor protein to gp 220/200.

EXAMPLE 2

Determination of Bam HIL DNA sequence which encodes the 3.4 kb and 2.8 kb RNAs

The Bam HIL DNA sequence which encodes the 3.4 and 2.8 kb RNAs was precisely defined by hybridization of polyadenylated B95-8 cytoplasmic RNA to separated strands of Bam HIL DNA. Bam HIL DNA was inserted into the pKH 47 plasmid (Gene 11: 109-115, 1980) and the strands separated by homopolymer chromatography as previously described (J. Virol. 46: 424-433, 1983). The conditions of hybridization, Sl nuclease degradation of unhybridized DNA and size determination of the Sl resistant DNA which was protected by the RNA are also previously described (J. Virol. 46: 424-433, 1983). The RNA hybridized to continuous 3.4 and 2.8 kb segments of the L strand of EBV DNA (the L strand has its 5' end to the left in the genome map shown in PNAS 77: 2999-3003, 1980 and J. Virol. 46: 424-433, 1983). The 3.4 and 2.8 kb exons defined above were mapped within the Bam HIL fragment using an EcoRI restriction endonuclease site which is approximately 1.3 kb from the right end of the Bam HIL fragment. Cleavage of the pKH 47 Bam HIL recombinant plasmid with EcoRI leaves 3.8 kb of the Bam HIL L strand attached to the PKH 47 homopolymer tail so that this part of the L strand of the Bam HIL fragment can be separated. The B95-8 cytoplasmic polyadenylated RNA hybridized to a continuous 2.1 kb segment of EcoRI cut Bam HIL L strand DNA. This result indicates that the 2.8 and 3.4 kb exons have a common end which is 2.1 kb to the left of the EcoRI site defined above. A PstI restriction endonuclease fragment of Bam HIL DNA which extends from 1870 nucleotides to the left to 40 nucleotides to the right of the EcoRI site hybridizes to 4.75, 3.4 and 2.8 kb RNAs in blots of B95-8 cytoplasmic polyadenylated RNA (J. Virol. 43: 262-272, 1982) indicating that the 3.4 and 2.8 kb DNAs encode part of the 4.75, 3.4 and 2.8 kb RNAs. The boundaries of the 4.75, 3.4 and 2.8 kb RNAs were further defined by RNA blot hybridizations with probes made from M13 clones (derived in Example 3 following). In these experiments it was demonstrated that:

(i) The 4.75 kb RNA hybridizes to probes from the left end of Bam HIE, and to probes extending approximately 3.4 kb into BAM HIL.

(ii) The 3.4 kb RNA hybridizes only to probes which include the DNA sequence complementary to that shown in Example 3 following. Probes from fragments 6 kb or 4 kb to right or left of the sequence shown in Example 3 did not hybridize to the 3.4 kb RNA indicating that the nonpolyadenylated component of the 3.4 kb RNA is 2.8 kb or there are multiple small exons which are not detected in the blot hybridizations. (There could be an error of ±10% in the size of the 3.4 kg RNA.)

(iii) The 2.8 kb RNA also hybridized only to probes complementary to the DNA sequence shown in Example 3. In this instance a M13 derived probe complementary to the sequence extending from nucleotide 1534 to nucleotide 1586 failed to hybridize to the RNA revealing an intron. M13 clones around the intron sequence defined in the previous experiment were used to define a splice donor site at nucleotide 1501 and an acceptor site at nucleotide 2092 in Example 3 below. S1 mapping experiments using labeled DNA probes made from M13 clones derived in Example 3 further define the 5' and 3' ends of the 3.4 and 2.8 kb RNAs to be 15 nucleotides 5' and 43 nucleotides 3' to the sequence shown in Example 3.

There is an obvious discrepancy between the number of codons (907) in the 2721 b open reading frame and the apparent size (135 kd) of the protein encoded by the 3.4 kb RNA. If the 2721 b open reading frame described in Example 3 encodes the entire 135 kd precursor of gp 350/300, the size of the precursor must be 95 kd and the apparent size of 135 kd must be due to anomalous behavior of the protein on SDS polyacrylamide gels. To investigate the behavior of this protein in SDS polyacrylamide gels, the initial B-galactosidase fusion protein described in Example 4 was analyzed on SDS polyacrylamide gels. Although the size of the fusion protein is 169 kd (116 for Beta-galactosidase plus 53 kd for the EBV insert), the apparent size of the protein was 190 kd in 6% SDS polyacrylamide gels. The 53 kd EBV part of the fusion protein was produced by inserting a stop codon after the EBV insert of the recombinant clone. The apparent size of this 54 kd EBV protein (with the first seven amino acids of Beta-galactosidase) was 84 kd in SDS polyacrylamide gels or 1.5 times its actual size. Thus, the 95 kd translation product of the 907 codon open reading frame is likely to be the entire protein which has an apparent size of 135 kd in SDS polyacrylamide gels.

EXAMPLE 3

Determination of Nucleotide Sequence of the 2.8 kb EBV DNA

The nucleotide sequence of the 2.8 kb EBV DNA fragment defined in Example 2 was determined by M13-dideoxy sequencing as previously described (Nucl. Acids Res. 9: 309–321, 1981; PNAS 74: 5463–5467, 1967). The important characteristic of the 2.8 kb nucleotide sequence is that it has a single long open reading frame which ends before a polyadenylation site at 3300 nucleotides 3' from the rightward Bam HIL site. The 2.8 kb DNA segment encodes a 95 kd protein which as shown in Example 2 migrates anomalously during electrophoresis on SDS polyacrylamide gels and is the 135 kd protein described in Example 1.

A. The nucleotide sequence of the 2.8 kb EBV DNA fragment and the amino acid sequence of the 95 kd protein encoded by this nucleotide sequence are given below.

| ATG | GAG | GCA | GCC | TTG | CTT | GTG | TGT | CAG | TAC | ACC | ATC | CAG | AGC |
|---|---|---|---|---|---|---|---|---|---|---|---|---|---|
| Met | Glu | Ala | Ala | Leu | Leu | Val | Cys | Gln | Tyr | Thr | Ile | Gln | Ser |
| CTG | ATC | CAT | CTC | ACG | GGT | GAA | GAT | CCT | GGT | TTT | TTC | AAT | GTT |
| Leu | Ile | His | Leu | Thr | Gly | Glu | Asp | Pro | Gly | Phe | Phe | Asn | Val |
| GAG | ATT | CCG | GAA | TTC | CCA | TTT | TAC | CCC | ACA | TGC | AAT | GTT | TGC |
| Glu | Ile | Pro | Glu | Phe | Pro | Phe | Tyr | Pro | Thr | Cys | Asn | Val | Cys |
| ACG | GCA | GAT | GTC | AAT | GTA | ACT | ATC | AAT | TTC | GAT | GTC | GGG | GGC |
| Thr | Ala | Asp | Val | Asn | Val | Thr | Ile | Asn | Phe | Asp | Val | Gly | Gly |
| AAA | AAG | CAT | CAA | CTT | GAT | CTT | GAC | TTT | GGC | CAG | CTG | ACA | CCC |
| Lys | Lys | His | Gln | Leu | Asp | Leu | Asp | Phe | Gly | Gln | Leu | Thr | Pro |
| CAT | ACG | AAG | GCT | GTC | TAC | CAA | CCT | CGA | GGT | GCA | TTT | GGT | GGC |
| His | Thr | Lys | Ala | Val | Tyr | Gln | Pro | Arg | Gly | Ala | Phe | Gly | Gly |
| TCA | GAA | AAT | GCC | ACC | AAT | CTC | TTT | CTA | CTG | GAG | CTC | CTT | GGT |
| Ser | Glu | Asn | Ala | Thr | Asn | Leu | Phe | Leu | Leu | Glu | Leu | Leu | Gly |
| GCA | GGA | GAA | TTG | GCT | CTA | ACT | ATG | CGG | TCT | AAG | AAG | CTT | CCA |
| Ala | Gly | Glu | Leu | Ala | Leu | Thr | Met | Arg | Ser | Lys | Lys | Leu | Pro |
| ATT | AAC | GTC | ACC | ACC | GGA | GAG | GAG | CAA | CAA | GTA | AGC | CTG | GAA |
| Ile | Asn | Val | Thr | Thr | Gly | Glu | Glu | Gln | Gln | Val | Ser | Leu | Glu |
| TCT | GTA | GAT | GTC | TAC | TTT | CAA | GAT | GTG | TTT | GGA | ACC | ATG | TGG |
| Ser | Val | Asp | Val | Tyr | Phe | Gln | Asp | Val | Phe | Gly | Thr | Met | Trp |
| TGC | CAC | CAT | GCA | GAA | ATG | CAA | AAC | CCC | GTG | TAC | CTG | ATA | CCA |
| Cys | His | His | Ala | Glu | Met | Gln | Asn | Pro | Val | Tyr | Leu | Ile | Pro |
| GAA | ACA | GTG | CCA | TAC | ATA | AAG | TGG | GAT | AAC | TGT | AAT | TCT | ACC |
| Glu | Thr | Val | Pro | Tyr | Ile | Lys | Trp | Asp | Asn | Cys | Asn | Ser | Thr |
| AAT | ATA | ACG | GCA | GTA | GTG | AGG | GCA | CAG | GGG | CTG | GAT | GTC | ACG |
| Asn | Ile | Thr | Ala | Val | Val | Arg | Ala | Gln | Gly | Leu | Asp | Val | Thr |
| CTA | CCC | TTA | AGT | TTG | CCA | ACG | TCA | GCT | CAA | GAC | TCG | AAT | TTC |
| Leu | Pro | Leu | Ser | Leu | Pro | Thr | Ser | Ala | Gln | Asp | Ser | Asn | Phe |
| AGC | GTA | AAA | ACA | GAA | ATG | CTC | GGT | AAT | GAG | ATA | GAT | ATT | GAG |
| Ser | Val | Lys | Thr | Glu | Met | Leu | Gly | Asn | Glu | Ile | Asp | Ile | Glu |
| TGT | ATT | ATG | GAG | GAT | GGC | GAA | ATT | TCA | CAA | GTT | CTG | CCC | GGA |
| Cys | Ile | Met | Glu | Asp | Gly | Glu | Ile | Ser | Gln | Val | Leu | Pro | Gly |
| GAC | AAC | AAA | TTT | AAC | ATC | ACC | TGC | AGT | GGA | TAC | GAG | AGC | CAT |
| Asp | Asn | Lys | Phe | Asn | Ile | Thr | Cys | Ser | Gly | Tyr | Glu | Ser | His |
| GTT | CCC | AGC | GGC | GGA | ATT | CTC | ACA | TCA | ACG | AGT | CCC | GTG | GCC |
| Val | Pro | Ser | Gly | Gly | Ile | Leu | Thr | Ser | Thr | Ser | Pro | Val | Ala |
| ACC | CCA | ATA | CCT | GGT | ACA | GGG | TAT | GCA | TAC | AGC | CTG | CGT | CTG |
| Thr | Pro | Ile | Pro | Gly | Thr | Gly | Tyr | Ala | Tyr | Ser | Leu | Arg | Leu |
| ACA | CCA | CGT | CCA | GTG | TCA | CGA | TTT | CTT | GGC | AAT | AAC | AGT | ATC |
| Thr | Pro | Arg | Pro | Val | Ser | Arg | Phe | Leu | Gly | Asn | Asn | Ser | Ile |
| CTG | TAC | GTG | TTT | TAC | TCT | GGG | AAT | GGA | CCG | AAG | GCG | AGC | GGG |

-continued

| | | | | | | | | | | | | | |
|---|---|---|---|---|---|---|---|---|---|---|---|---|---|
| Leu | Tyr | Val | Phe | Tyr | Ser | Gly | Asn | Gly | Pro | Lys | Ala | Ser | Gly |
| GGA | GAT | TAC | TGC | ATT | CAG | TCC | AAC | ATT | GTG | TTC | TCT | GAT | GAG |
| Gly | Asp | Tyr | Cys | Ile | Gln | Ser | Asn | Ile | Val | Phe | Ser | Asp | Glu |
| ATT | CCA | GCT | TCA | CAG | GAC | ATG | CCG | ACA | AAC | ACC | ACA | GAC | ATC |
| Ile | Pro | Ala | Ser | Gln | Asp | Met | Pro | Thr | Asn | Thr | Thr | Asp | Ile |
| ACA | TAT | GTG | GGT | GAC | AAT | GCT | ACC | TAT | TCA | GTG | CCA | ATG | GTC |
| Thr | Tyr | Val | Gly | Asp | Asn | Ala | Thr | Tyr | Ser | Val | Pro | Met | Val |
| ACT | TCT | GAG | GAC | GCA | AAC | TCG | CCA | AAT | GTT | ACA | GTG | ACT | GCC |
| Thr | Ser | Glu | Asp | Ala | Asn | Ser | Pro | Asn | Val | Thr | Val | Thr | Ala |
| TTT | TGG | GCC | TGG | CCA | AAC | AAC | ACT | GAA | ACT | GAC | TTT | AAG | TGC |
| Phe | Trp | Ala | Trp | Pro | Asn | Asn | Thr | Glu | Thr | Asp | Phe | Lys | Cys |
| AAA | TGG | ACT | CTC | ACC | TCG | GGG | ACA | CCT | TCG | GGT | TGT | GAA | AAT |
| Lys | Trp | Thr | Leu | Thr | Ser | Gly | Thr | Pro | Ser | Gly | Lys | Glu | Asn |
| ATT | TCT | GGT | GCA | TTT | GCG | AGC | AAT | CGG | ACA | TTT | GAC | ATT | ACT |
| Ile | Ser | Gly | Ala | Phe | Ala | Ser | Asn | Arg | Thr | Phe | Asp | Ile | Thr |
| GTC | TCG | GGT | CTT | GGC | ACG | GCC | CCC | AAG | ACA | CTC | ATT | ATC | ACA |
| Val | Ser | Gly | Leu | Gly | Thr | Ala | Pro | Lys | Thr | Leu | Ile | Ile | Thr |
| CGA | ACG | GCT | ACC | AAT | GCC | ACC | ACA | ACA | ACC | CAC | AAG | GTT | ATA |
| Arg | Thr | Ala | Thr | Asn | Ala | Thr | Thr | Thr | Thr | His | Lys | Val | Ile |
| TTC | TCC | AAG | GCA | CCC | GAG | AGC | ACC | ACC | ACC | TCC | CCT | ACC | TTG |
| Phe | Ser | Lys | Ala | Pro | Glu | Ser | Thr | Thr | Thr | Ser | Pro | Thr | Leu |
| AAT | ACA | ACT | GGA | TTT | GCT | GAT | CCC | AAT | ACA | ACG | ACA | GGT | CTA |
| Asn | Thr | Thr | Gly | Phe | Ala | Asp | Pro | Asn | Thr | Thr | Thr | Gly | Leu |
| CCC | AGC | TCT | ACT | CAC | GTG | CCT | ACC | AAC | CTC | ACC | GCA | CCT | GCA |
| Pro | Ser | Ser | Thr | His | Val | Pro | Thr | Asn | Leu | Thr | Ala | Pro | Ala |
| AGC | ACA | GGC | CCC | ACT | GTA | TCC | ACC | GCG | GAT | GTC | ACC | AGC | CCA |
| Ser | Thr | Gly | Pro | Thr | Val | Ser | Thr | Ala | Asp | Val | Thr | Ser | Pro |
| ACA | CCA | GCC | GGC | ACA | ACG | TCA | GGC | GCA | TCA | CCG | GTG | ACA | CCA |
| Thr | Pro | Ala | Gly | Thr | Thr | Ser | Gly | Ala | Ser | Pro | Val | Thr | Pro |
| AGT | CCA | TCT | CCA | TGG | GAC | AAC | GGC | ACA | GAA | AGT | AAG | GCC | CCC |
| Ser | Pro | Ser | Pro | Trp | Asp | Asn | Gly | Thr | Glu | Ser | Lys | Ala | Pro |
| GAC | ATG | ACC | AGC | TCC | ACC | TCA | CCA | GTG | ACT | ACC | CCA | ACC | CCA |
| Asp | Met | Thr | Ser | Ser | Thr | Ser | Pro | Val | Thr | Thr | Pro | Thr | Pro |
| AAT | GCC | ACC | AGC | CCC | ACC | CCA | GCA | GTG | ACT | ACC | CCA | ACC | CCA |
| Asn | Ala | Thr | Ser | Pro | Thr | Pro | Ala | Val | Thr | Thr | Pro | Thr | Pro |
| AAT | GCC | ACC | AGC | CCC | ACC | CCA | GCA | GTG | ACT | ACC | CCA | ACC | CCA |
| Asn | Ala | Thr | Ser | Pro | Thr | Pro | Ala | Val | Thr | Thr | Pro | Thr | Pro |
| AAT | GCC | ACC | AGC | CCC | ACC | TTG | GGA | AAA | ACA | AGT | CCT | ACC | TCA |
| Asn | Ala | Thr | Ser | Pro | Thr | Leu | Gly | Lys | Thr | Ser | Pro | Thr | Ser |
| GCA | GTG | ACT | ACC | CCA | ACC | CCA | AAT | GCC | ACC | AGC | CCC | ACC | TTG |
| Ala | Val | Thr | Thr | Pro | Thr | Pro | Asn | Ala | Thr | Ser | Pro | Thr | Leu |
| GGA | AAA | ACA | AGC | CCC | ACC | TCA | GCA | GTG | ACT | ACC | CCA | ACC | CCA |
| Gly | Lys | Thr | Ser | Pro | Thr | Ser | Ala | Val | Thr | Thr | Pro | Thr | Pro |
| AAT | GCC | ACC | AGC | CCC | ACC | TTG | GGA | AAA | ACA | AGC | CCC | ACC | TCA |
| Asn | Ala | Thr | Ser | Pro | Thr | Leu | Gly | Lys | Thr | Ser | Pro | Thr | Ser |
| GCA | GTG | ACT | ACC | CCA | ACC | CCA | AAT | GCC | ACC | GGC | CCT | ACT | GTG |
| Ala | Val | Thr | Thr | Pro | Thr | Pro | Asn | Ala | Thr | Gly | Pro | Thr | Val |
| GGA | GAA | ACA | AGT | CCA | CAG | GCA | AAT | GCC | ACC | AAC | CAC | ACC | TTA |
| Gly | Glu | Thr | Ser | Pro | Gln | Ala | Asn | Ala | Thr | Asn | His | Thr | Leu |
| GGA | GGA | ACA | AGT | CCC | ACC | CCA | GTA | GTT | ACC | AGC | CAA | CCA | AAA |
| Gly | Gly | Thr | Ser | Pro | Thr | Pro | Val | Val | Thr | Ser | Gln | Pro | Lys |
| AAT | GCA | ACC | AGT | GCT | GTT | ACC | ACA | GGC | CAA | CAT | AAC | ATA | ACT |
| Asn | Ala | Thr | Ser | Ala | Val | Thr | Thr | Gly | Gln | His | Asn | Ile | Thr |
| TCA | AGT | TCA | ACC | TCT | TCC | ATG | TCA | CTG | AGA | CCC | AGT | TCA | AAC |
| Ser | Ser | Ser | Thr | Ser | Ser | Met | Ser | Leu | Arg | Pro | Ser | Ser | Asn |
| CCA | GAG | ACA | CTC | AGC | CCC | TCC | ACC | AGT | GAC | AAT | TCA | ACG | TCA |
| Pro | Glu | Thr | Leu | Ser | Pro | Ser | Thr | Ser | Asp | Asn | Ser | Thr | Ser |
| CAT | ATG | CCT | TTA | CTA | ACC | TCC | GCT | CAC | CCA | ACA | GGT | GGT | GAA |
| His | Met | Pro | Leu | Leu | Thr | Ser | Ala | His | Pro | Thr | Gly | Gly | Glu |
| AAT | ATA | ACA | CAG | GTG | ACA | CCA | GCC | TCT | ATC | AGC | ACA | CAT | CAT |
| Asn | Ile | Thr | Gln | Val | Thr | Pro | Ala | Ser | Ile | Ser | Thr | His | His |
| GTG | TCC | ACC | AGT | TCG | CCA | GAA | CCC | CGC | CCA | GGC | ACC | ACC | AGC |
| Val | Ser | Thr | Ser | Ser | Pro | Glu | Pro | Arg | Pro | Gly | Thr | Thr | Ser |
| CAA | GCG | TCA | GGC | CCT | GGA | AAC | AGT | TCC | ACA | TCC | ACA | AAA | CCG |
| Gln | Ala | Ser | Gly | Pro | Gly | Asn | Ser | Ser | Thr | Ser | Thr | Lys | Pro |
| GGG | GAG | GTT | AAT | GTC | ACC | AAA | GGC | ACG | CCC | CCC | CAA | AAT | GCA |
| Gly | Glu | Val | Asn | Val | Thr | Lys | Gly | Thr | Pro | Pro | Gln | Asn | Ala |
| ACG | TCG | CCC | CAG | GCC | CCC | AGT | GGC | CAA | AAG | ACG | GCG | GTT | CCC |
| Thr | Ser | Pro | Gln | Ala | Pro | Ser | Gly | Gln | Lys | Thr | Ala | Val | Pro |
| ACG | GTC | ACC | TCA | ACA | GGT | GGA | AAG | GCC | AAT | TCT | ACC | ACC | GGT |
| Thr | Val | Thr | Ser | Thr | Gly | Gly | Lys | Ala | Asn | Ser | Thr | Thr | Gly |
| GGA | AAG | CAC | ACC | ACA | GGA | CAT | GGA | GCC | CGG | ACA | AGT | ACA | GAG |
| Gly | Lys | His | Thr | Thr | Gly | His | Gly | Ala | Arg | Thr | Ser | Thr | Glu |
| CCC | ACC | ACA | GAT | TAC | GGC | GGT | GAT | TCA | ACT | ACG | CCA | AGA | CCG |
| Pro | Thr | Thr | Asp | Tyr | Gly | Gly | Asp | Ser | Thr | Thr | Pro | Arg | Pro |
| AGA | TAC | AAT | GCG | ACC | ACC | TAT | CTA | CCT | CCC | AGC | ACT | TCT | AGC |
| Arg | Tyr | Asn | Ala | Thr | Thr | Tyr | Leu | Pro | Pro | Ser | Thr | Ser | Ser |
| AAA | CTG | CGG | CCC | CGC | TGG | ACT | TTT | ACG | AGC | CCA | CCG | GTT | ACC |
| Lys | Leu | Arg | Pro | Arg | Trp | Thr | Phe | Thr | Ser | Pro | Pro | Val | Thr |
| ACA | GCC | CAA | GCC | ACC | GTG | CCA | GTC | CCG | CCA | ACG | TCC | CAG | CCC |
| Thr | Ala | Gln | Ala | Thr | Val | Pro | Val | Pro | Pro | Thr | Ser | Gln | Pro |
| AGA | TTC | TCA | AAC | CTC | TCC | ATG | CTA | GTA | CTG | CAG | TGG | GCC | TCT |

| Arg | Phe | Ser | Asn | Leu | Ser | Met | Leu | Val | Leu | Gln | Trp | Ala | Ser |
|---|---|---|---|---|---|---|---|---|---|---|---|---|---|
| CTG | GCT | GTG | CTG | ACC | CTT | CTG | CTG | CTG | CTG | GTC | ATG | GCG | GAC |
| Leu | Ala | Val | Leu | Thr | Leu | Leu | Leu | Leu | Leu | Val | Met | Ala | Asp |
| TGC | GCC | TTT | AGG | CGT | AAC | TTG | TCT | ACA | TCC | CAT | ACC | TAC | ACC |
| Cys | Ala | Phe | Arg | Arg | Asn | Leu | Ser | Thr | Ser | His | Thr | Tyr | Thr |
| ACC | CCA | CCA | TAT | GAT | GAC | GCC | GAG | ACC | TAT | GTA | | | |
| Thr | Pro | Pro | Tyr | Asp | Asp | Ala | Glu | Thr | Tyr | Val | | | |

EXAMPLE 4

Sequence Cloning, Expression and Immuno Characterization of Peptides Expressed by Nucleotide Sequence of the 2.8 kb EBV DNA Fragments The sequence as defined above is demonstrated to contain immunogenic epitopes recognized by humans in their antibody response to EBV infection. The DNA segment between the PstI sites defined in Example 2 and the DNA segment between the EcoRI site also defined in Example 2 and an EcoRI site to the right of this site were cloned into the B-galactosidase expression vector pMC 1511 and inserted into *E. coli* using strategies and procedures described in PNAS 80: 5665–5669, 1983. The recombinant clones were selected for B-galactosidase (B-gal) activity, for the content of EBV Bam HIL DNA, and for the production of hybrid B-gal-EBV proteins using the methods described above. Colonies stably expressing fusion proteins of the expected size were propagated and checked for immunoreactivity with human sera containing antibody to EBV membrane antigens as previously described (PNAS 80: 5665–5669, 1983 and Example 2). Fusion proteins were purified from ammonium sulfate fractionated *E. coli* cell lysates (as described in PNAS: 80: 6848–6852, 1983) using B-gal affinity chromatography or Sephacryl columns. Rabbits were immunized subcutaneously with three injections at 2-week intervals of 200 μg of a purified EBV beta galactosidase fusion protein. The first injection contained Freund's complete adjuvant; the second and third injections contained Freund's incomplete adjuvant. Bleeding was done 2 weeks after the third injection. The EBV protein insertion clone used to immunize rabbits begins at the Ile Gln Ser Asn Ile Val starting at nucleotide 894 (amino acid 299) of Example 3A and ends with Asp Tyr Gly Gly Asp Ser ending at nucleotide 2422 (amino acid 807) of Example 3A. Immune serum from the rabbits reacts with gp 350 and gp 220 in extracts of EBV infected cells using immuno-blot procedures described in PNAS 80: 5665–5669, 1983 and also reacts with the outer plasma membrane of EBV infected cells. The rabbit antisera reacts only with the outer plasma membrane of EBV infected cells which are active in virus replication and in the synthesis and insertion into the cell plasma membrane of the virus membrane proteins.

The immunization of rabbits was continued at two week intervals with subcutaneous injection of 400 μg of alum absorbed EBV Beta-galactosidase fusion protein. Reactivity of the rabbit sera with membrane antigens on the surface of virus producing B95-8 cells increased after each of eleven injections. The rabbit sera were demonstrated to immunoprecipitate gp 350/300 and 220/200 from nonionic detergent extracts of B95-8 or P3Hr-1 cells which had been induced to produce virus and to neutralize the human lymphocyte infectivity of EBV.

Mice were immunized with three injections of 200 μg of alum absorbed Beta-galactosidase fusion proteins. After the second and third injection a 1:5 dilution of sera from the immunized mice neutralized 90% of the P3HR-1 strain of EBV. In these experiments, a 1:10 dilution of virus from supernatants of induced cultures were assayed by infection of Raji cells (Virology, 102: 360–369).

Additional studies of the expression in *E. coli* of the 2721 b open reading frame shown in Example 3 demonstrated that more of the open reading frame could be expressed as a stable fusion protein in bacteria. The XhoII-ScaI fragment which begins at page 12, line 15, nucleotide 22 and ends at page 17, line 28, nucleotide 26 was digested with Bal 31 for 30 seconds at 30° C. and cloned into pMC 1513. The clone expressing the largest fusion protein was identified to be 1513XSRD6. This clone expresses a stable fusion protein of 220 kd. The EBV DNA insert in this clone begins about 40 nucleotides from the XhoII site and ends approximately 100 nucleotides from the ScaI site. The entire XhoII-ScaI fragment was also expressed as a stable lacz fusion protein of 250 kd in a similar expression vector in *E. coli*. Since the smaller part of the natural gp 350/300 precursor protein expressed as a beta-galactosidase fusion protein induces antibodies which react with the outer membranes of virus and virus infected cells and neutralize virus (as described earlier in this example), it is obvious that the larger protein has these properties and is a superior immunogen.

What is claimed is:

1. A polypeptide having the amino acid sequence:

Met Glu Ala Ala Leu Leu Val Cys Gln Tyr Thr Ile Gln Ser
Leu Ile His Leu Thr Gly Glu Asp Pro Gly Phe Phe Asn Val
Glu Ile Pro Glu Phe Pro Phe Tyr Pro Thr Cys Asn Val Cys
Thr Ala Asp Val Asn Val Thr Ile Asn Phe Asp Val Gly Gly
Lys Lys His Gln Leu Asp Leu Asp Phe Gly Gln Leu Thr Pro
His Thr Lys Ala Val Tyr Gln Pro Arg Gly Ala Phe Gly Gly
Ser Glu Asn Ala Thr Asn Leu Phe Leu Leu Glu Leu Leu Gly
Ala Gly Glu Leu Ala Leu Thr Met Arg Ser Lys Lys Leu Pro
Ile Asn Val Thr Thr Gly Glu Glu Gln Gln Val Ser Leu Glu
Ser Val Asp Val Tyr Phe Gln Asp Val Phe Gly Thr Met Trp
Cys His His Ala Glu Met Gln Asn Pro Val Tyr Leu Ile Pro
Glu Thr Val Pro Tyr Ile Lys Trp Asp Asn Cys Asn Ser Thr
Asn Ile Thr Ala Val Val Arg Ala Gln Gly Leu Asp Val Thr
Leu Pro Leu Ser Leu Pro Thr Ser Ala Gln Asp Ser Asn Phe
Ser Val Lys Thr Glu Met Leu Gly Asn Glu Ile Asp Ile Glu
Cys Ile Met Glu Asp Gly Glu Ile Ser Gln Val Leu Pro Gly
Asp Asn Lys Phe Asn Ile Thr Cys Ser Gly Tyr Glu Ser His
Val Pro Ser Gly Gly Ile Leu Thr Ser Thr Ser Pro Val Ala
Thr Pro Ile Pro Gly Thr Gly Tyr Ala Tyr Ser Leu Arg Leu
Thr Pro Arg Pro Val Ser Arg Phe Leu Gly Asn Asn Ser Ile
Leu Tyr Val Phe Tyr Ser Gly Asn Gly Pro Lys Ala Ser Gly
Gly Asp Tyr Cys Ile Gln Ser Asn Ile Val Phe Ser Asp Glu
Ile Pro Ala Ser Gln Asp Met Pro Thr Asn Thr Thr Asp Ile
Thr Tyr Val Gly Asp Asn Ala Thr Tyr Ser Val Pro Met Val
Thr Ser Glu Asp Ala Asn Ser Pro Asn Val Thr Val Thr Ala
Phe Trp Ala Trp Pro Asn Asn Thr Glu Thr Asp Phe Lys Cys
Lys Trp Thr Leu Thr Ser Gly Thr Pro Ser Gly Lys Glu Asn
Ile Ser Gly Ala Phe Ala Ser Asn Arg Thr Phe Asp Ile Thr
Val Ser Gly Leu Gly Thr Ala Pro Lys Thr Leu Ile Ile Thr
Arg Thr Ala Thr Asn Ala Thr Thr Thr Thr His Lys Val Ile
Phe Ser Lys Ala Pro Glu Ser Thr Thr Thr Ser Pro Thr Leu
Asn Thr Thr Gly Phe Ala Asp Pro Asn Thr Thr Thr Gly Leu
Pro Ser Ser Thr His Val Pro Thr Asn Leu Thr Ala Pro Ala

Ser Thr Gly Pro Thr Val Ser Thr Ala Asp Val Thr Ser Pro
Thr Pro Ala Gly Thr Thr Ser Gly Ala Ser Pro Val Thr Pro
Ser Pro Ser Pro Trp Asp Asn Gly Thr Glu Ser Lys Ala Pro
Asp Met Thr Ser Ser Thr Ser Pro Val Thr Thr Pro Thr Pro
Asn Ala Thr Ser Pro Thr Pro Ala Val Thr Thr Pro Thr Pro
Asn Ala Thr Ser Pro Thr Pro Ala Val Thr Thr Pro Thr Pro
Asn Ala Thr Ser Pro Thr Leu Gly Lys Thr Ser Pro Thr Ser
Ala Val Thr Thr Pro Thr Pro Asn Ala Thr Ser Pro Thr Leu
Gly Lys Thr Ser Pro Thr Ser Ala Val Thr Thr Pro Thr Pro
Asn Ala Thr Ser Pro Thr Leu Gly Lys Thr Ser Pro Thr Ser
Ala Val Thr Thr Pro Thr Pro Asn Ala Thr Gly Pro Thr Val
Gly Glu Thr Ser Pro Gln Ala Asn Ala Thr Asn His Thr Leu
Gly Gly Thr Ser Pro Thr Pro Val Val Thr Ser Gln Pro Lys
Asn Ala Thr Ser Ala Val Thr Thr Gly Gln His Asn Ile Thr
Ser Ser Ser Thr Ser Ser Met Ser Leu Arg Pro Ser Ser Asn
Pro Glu Thr Leu Ser Pro Ser Thr Ser Asp Asn Ser Thr Ser
His Met Pro Leu Leu Thr Ser Ala His Pro Thr Gly Gly Glu
Asn Ile Thr Gln Val Thr Pro Ala Ser Ile Ser Thr His His

-continued

Val Ser Thr Ser Ser Pro Glu Pro Arg Pro Gly Thr Thr Ser Gln Ala Ser Gly Pro Gly Asn Ser Ser Thr Ser Thr Lys Pro Gly Glu Val Asn Val Thr Lys Gly Thr Pro Pro Gln Asn Ala Thr Ser Pro Gln Ala Pro Ser Gly Gln Lys Thr Ala Val Pro Thr Val Thr Ser Thr Gly Gly Lys Ala Asn Ser Thr Thr Gly Gly Lys His Thr Thr Gly His Gly Ala Arg Thr Ser Thr Glu Pro Thr Thr Asp Tyr Gly Gly Asp Ser Thr Thr Pro Arg Pro Arg Tyr Asn Ala Thr Thr Tyr Leu Pro Pro Ser Thr Ser Ser Lys Leu Arg Pro Arg Trp Thr Phe Thr Ser Pro Pro Val Thr Thr Ala Gln Ala Thr Val Pro Val Pro Pro Thr Ser Gln Pro Arg Phe Ser Asn Leu Ser Met Leu Val Leu Gln Trp Ala Ser Leu Ala Val Leu Thr Leu Leu Leu Leu Leu Val Met Ala Asp Cys Ala Phe Arg Arg Asn Leu Ser Thr Ser His Thr Tyr Thr Thr Pro Pro Tyr Asp Asp Ala Gly Thr Tyr Val

2. A composition comprising an immunologically effective amount of the peptide of claim 1 or an immunologically effective subunit thereof in a suitable carrier.

* * * * *

UNITED STATES PATENT AND TRADEMARK OFFICE
CERTIFICATE OF CORRECTION

PATENT NO.   :   4,707,358
DATED        :   November 17, 1987
INVENTOR(S)  :   Elliott Kieff, et al.

It is certified that error appears in the above-identified patent and that said Letters Patent is hereby corrected as shown below:

Column 1, line 7:

--ACKNOWLEDGMENT OF GOVERNMENT SUPPORT

This invention was made with government support under Grants CA 19264 and CA 17281 awarded by the National Institutes of Health. The government has certain rights in the invention.--

Signed and Sealed this

Twentieth Day of September, 1994

Attest:

BRUCE LEHMAN

*Attesting Officer*   *Commissioner of Patents and Trademarks*